United States Patent [19]
Axelsson et al.

[11] Patent Number: 5,981,539
[45] Date of Patent: Nov. 9, 1999

[54] PIPERIDINE COMPOUNDS AS CALCIUM CHANNEL BLOCKERS

[75] Inventors: Oskar Axelsson, Malmo; Dan Peters, Arlov, both of Sweden; Nielsen Elsebet Østergaard, Copenhagen; Palle Christophersen, Ballerup, both of Denmark

[73] Assignee: Neurosearch A/S, Glostrup, Denmark

[21] Appl. No.: 09/029,773

[22] PCT Filed: Sep. 13, 1996

[86] PCT No.: PCT/EP96/04039

§ 371 Date: May 29, 1998

§ 102(e) Date: May 29, 1998

[87] PCT Pub. No.: WO97/10212

PCT Pub. Date: Mar. 20, 1997

[30] Foreign Application Priority Data

Sep. 15, 1995 [DK] Denmark .................................. 1025/95

[51] Int. Cl.[6] ...................... A61K 31/445; C07D 211/42; C07D 211/46
[52] U.S. Cl. .......................... 514/278; 514/327; 514/328; 546/19; 546/216; 546/217; 546/219; 546/220; 546/222
[58] Field of Search ...................... 546/216, 217, 546/222, 219, 220, 19; 514/327, 328, 278

[56] References Cited

U.S. PATENT DOCUMENTS 4,160,837  7/1979  Paioni ........................ 424/267
4,994,471  2/1991  Lalinde et al. ................... 514/326

FOREIGN PATENT DOCUMENTS

2738477A1  3/1978  Germany .
WO 9202502  2/1992  WIPO .

OTHER PUBLICATIONS

Van Daele et al., *Drug Development Research*, vol. 8, pp. 225–232 (1986).

*Primary Examiner*—Evelyn Mei Huang
*Attorney, Agent, or Firm*—Birch, Stewart, Kolasch & Birch, LLP

[57] ABSTRACT

The present invention discloses compounds of the formula

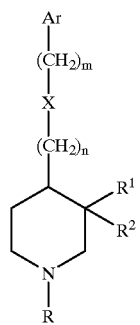

any of its enantiomers or any mixture thereof, or a pharmaceutically-acceptable addition salt thereof, wherein X, Ar, R, $R^1$, $R^2$, n are as defined herein.

8 Claims, No Drawings

PIPERIDINE COMPOUNDS AS CALCIUM CHANNEL BLOCKERS

This application is the national phase under 35 U.S.C. §371 of prior PCT International Application No. PCT/EP96/04039 which has an International filing date of Sep. 13, 1996 which designated the United States of America, published as WO 97/10212 on Mar. 20, 1997, the entire contents of which are hereby incorporated by reference.

The present invention relates to pharmaceutically active compounds and their use as well as to pharmaceutical preparations comprising the compounds. The compounds of the invention possess valuable activity as calcium channel blockers which make them useful in the treatment of stroke, anoxia, ischemia, migraine, psychosis (e.g. affective disorders), epilepsy or any other convulsive disorder.

It is well known that an accumulation of calcium (calcium overload) in the brain is seen after anoxia, ischemia, migraine and other hyperactivity periods of the brain, such as after epileptic convulsions. An uncontrolled high concentration of calcium in the cells of the Central Nervous System (CNS) is known to cause most of the degenerative changes connected with the above diseases. Compounds which can block the calcium channels of brain cells will therefore be useful in the treatment of anoxia, ischemia, migraine, epilepsia and in the prevention of the degenerative changes connected with same.

Compounds blocking the so called L-type calcium channels in the CNS will be useful for the treatment of the above disorders by directly blocking the calcium uptake in the CNS.

Further, it is well known that the so called N- and P-types of calcium channels, as well as possibly other types of calcium channels, are involved in the regulation of neurotransmitter release. Compounds blocking the N- and/or P-types of calcium channels will indirectly and very powerfully prevent calcium overload in the CNS after the hyperactivity periods of the brain as described above by inhibiting the enhanced neurotransmitter release seen after such hyperactivity periods of the CNS, and especially the neurotoxic, enhanced glutamate release after such hyperactivity periods of the CNS. Furthermore, blockers of the N- and/or P-types of calcium channels will as dependent upon the selectivity of the compound in question inhibit the release of various other neurotransmitters such as aspartate, GABA, glycine, dopamine, serotonin and noradrenaline.

DE-A-2738477 discloses the use of piperidine derivatives for the preparation of antidepressants.

U.S. Pat. No. 4,994,471 discloses piperidine derivatives which are useful as analgesics.

Drug Development Research 8, pages 225–232 (1986) discloses the synthesis of cisapride, a gastrointestinal stimulant derived from cis-4-amino-3-methoxypiperidine.

WO-A-92/02502 discloses processes for preparing piperidine derivatives, pharmaceutical compositions containing said compounds and their use in therapy, in particular as calcium blocking agents.

It is an object of the present invention to provide compounds capable of blocking the L-type and/or the N-type and/or the P-type of calcium channels, and/or other types of calcium channels.

In combination with their calcium channel blocking activity certain compounds of the invention also possess valuable sodium channel blocking activity.

The main pathway for the sodium ion in excitable cells is the voltage operated Na-channels. These channels are universally distributed in excitable cells such as neurons, skeletal—and heart muscles, as well as in various gland cells. Voltage-gated sodium channels are responsible for the initial, rapid depolarization of the action potential in nerve and muscle cells. At negative membrane potentials, most sodium channels are in closed, resting states. In response to membrane depolarization, the channels open for a few hundred microseconds, resulting in sodium-ion influx through a sodium-ion selective pore, and then convert to a nonconducting inactivated state. Modulation of sodium channels is the mechanism of action of local anesthetics and class I antiarrhytmics, and several antepileptic compounds exert their effects through a blockade of neuronal sodium channels in the CNS. Furthermore, it has been suggested that sodium influx is the first step in post-ischaemic neuronal damage and several sodium channel blockers have shown neuroprotective effect in animal models of ischaemia (Neuroscience Letters, 121(1991), pages 251–254, Brain Research, 652 (1994), pages 216–22, and J. Pharmacol Exp. Ther., Vol. 269, No. 2, 854–859 (1994)). Drugs such as Lifarizine, Lanodipine and Lomerizine that act at both sodium and calcium channels have been shown to possess powerful anti-ischaemic activity in animal models.

In a preferred embodiment of the invention, the degree of the calcium and/or sodium channel blockade of the compounds of the invention depends on the activity of the channel.

The invention then, inter alia, comprises the following, alone or in combination:

A compound having the formula

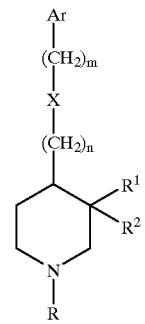

any of its enantiomers or any mixture thereof, or a pharmaceutically-acceptable addition salt thereof, wherein X is O, S, or $NR^3$, wherein $R^3$ is hydrogen, alkyl, or aryl which may be substituted one or more times with substitutents selected from the group consisting of alkyl, alkoxy, halogen, amino, nitro, cyano, trifluoromethyl, aryl, arylalkyl, aryloxy and arylalkyloxy;

m is 0,1, or 2;

n is 0,1, or 2;

R is cycloalkyl, cycloalkylalkyl, $(aryl)_p$-alkyl, $(aryl)_p$-alkenyl, or $(aryl)_p$-alkynyl, wherein the aryl group may be substituted one or more times with substitutents selected from the group consisting of alkyl, alkoxy, halogen, amino, nitro, cyano and trifluoromethyl, and 0, or 1;

one of $R^1$ and $R^2$ is —O—Z, or —S—Z, wherein Z is hydrogen; alkyl; alkenyl; alkynyl; cycloalkyl; cycloalkylalky; arylalkyl, arylalkenyl, arylalkenyl, or aryl-CO—, wherein the aryl groups may be substituted one or more times with substitutents selected from the group consisting of alkyl, alkoxy, halogen, amino, nitro, cyano and trifluoromethyl; or Z is —$(CH_2)_o$—

CO—R[6], —(CH$_2$)$_o$—COOR[6], —(CH$_2$)$_o$—CONR[6]R[7], or —(CH$_2$)$_o$—Het, wherein o is 0, 1, 2, 3, 4, or 5 and R[6] and R[7] each independently are hydrogen, or alkyl, and Het is a five or six membered monocyclic heterocyclic ring; or Z is —(CH$_2$)$_o$—WR[4], or

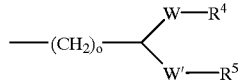

wherein o is 0,1, 2, 3, 4, or 5, W and W' each independently are O, or S, and R[4] and R[5] each independently are hydrogen, or alkyl, or wherein R[4] and R[5] together is —(CH$_2$)$_q$—, wherein q is 2, or 3; and the other of R[1] and R[2] is hydrogen, alkoxy, or alkoxyalkoxy; or R[1] and R[2] together form a chain —W—(CH$_2$)$_q$—W'—, wherein W and W' each independently are O, or S and q is 2, or 3; and Ar is aryl which may be substituted one or more times with substitutents selected from the group consisting of alkyl, alkoxy, halogen, amino, nitro, cyano, trifluoromethyl, aryl, arylalkyl, aryloxy, and arylalkyloxy;

with the proviso that said compound is not trans-3-hydroxy-4-(3,4-dimethylphenoxy)-1-methyl-piperidine-hydrochloride,
trans-3-hydroxy-4-phenylthio-1-methyl-piperidine,
cis/trans-3-methoxy-4-(3,4-dimethylphenoxy)-1-methyl-piperidine,
trans-3-hydroxy-4-(3,4-dimethylphenoxy)-1-propargyl-piperidine,
trans4-hydroxy-3-(3,4-dimethylphenoxy)-1-methyl-piperidine,
trans-3-hydroxy-4-(2-bromo4-methoxyphenoxy)-1-methyl-piperidine,
cis/trans-3-hydroxy-4-(2,3-dimethylphenoxy)-1-methyl-piperidine,
cis-3-hydroxy-4-(3,4-dimethylphenoxy)-1-methyl-piperidine,
cis/trans-3-hydroxy-4-(1-naphthyloxy)-1-methyl-piperidine,
cis/trans-3-hydroxy-4-(m-chlorophenoxy)-1-methyl-piperidine,
cis/trans-3-hydroxy-4-(5,6,7,8-tetrahydro-1-naphthyloxy)-1-methyl-piperidine,
cis/trans-3-hydroxy-4-(p-fluorophenoxy)-1-methyl-piperidine,
trans-3-acetoxy-4-(3,4-dimethylphenoxy)-1-methyl-piperidine,
trans-3-hydroxy-4-(p-trifluoromethylphenoxy)-1-methyl-piperidine,
cis/trans-3-methoxy-4-(2,3-dimethylphenoxy)-1-methyl-piperidine,
1-phenylmethyl-3-methoxy-4-phenylaminopiperidine, or
a compound having the formula

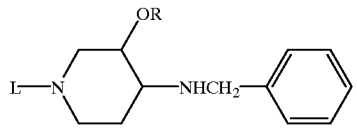

wherein R represents hydrogen or methyl and L is selected from —CH$_2$—Ph, —(CH$_2$)$_3$—CH(4F—Ph)$_2$, or ethyl, with Ph being phenyl;
a compound as above wherein R is alkyl, one of R[1] and R[2] is hydroxy, alkoxy, alkoxyalkoxy, or acyloxy and the other of R[1] and R[2] is hydrogen, or, alkoxy, or R[1] and R[2] together form —W—(CH$_2$)$_q$—W'—, wherein W and W' each independently are O, or S and q is 2, or 3; and n, m, X and Ar is as defined above;

a compound as above which is (±)-trans-4-[2-(3,4-Dichlorophenoxy)-ethyl]-3-methoxy-N-pentylpiperidine,
(±)-cis-4-[2-(2,3-Dimethylphenoxy)-ethyl]-3-methoxy-N-pentylpiperidine,
(±)-cis-4-[2-(3,4-Dichlorophenoxy)-ethyl]-3-ethoxy-(2-methoxy)-N-pentylpiperidine,
(±)-trans-4-[2-(3,4-Dichlorophenoxy)-ethyl]-3-ethoxy-(2-methoxy)-N-pentylpiperidine,
(±)-trans-4-[2-(3,4-Dichlorophenoxy)-ethyl]-3-acetoxy-N-pentylpiperidine,
(±)-trans-4-[2-(3-isopropoxyphenoxy) ethyl]-3-(2-methoxy-1-ethoxy)-N-pentylpiperidine,
(±)-trans-4-[4-phenoxyphenoxy]-3-(2-methoxy-1-ethoxy)-N-pentylpiperidine,
(±)-trans-4-[2-(N,N-diphenylamino)ethyl]-3-methoxy-N-pentylpiperidine,
(±)-cis-4-[2-(N,N-diphenylamino)ethyl]-3-methoxy-N-pentylpiperidine,
(±)-cis-4-[2-(2-phenylphenoxy)ethyl]-3-methoxy-N-pentylpiperidine,
(±)-trans-4-[(4-chlorobenzyl)thio]-3-(2-methoxy-1-ethoxy)-N-pentylpiperidine,
(±)-cis-4-[2-(2-benzylphenoxy)ethyl]-3-methoxy-N-pentylpiperidine,
(±)-trans-4-[2-(2-benzylphenoxy)ethyl]-3-methoxy-N-pentylpiperidine,
(±)-trans-4-[2-benzyloxyphenoxy]-3-(2-methoxy-1-ethoxy)-N-pentylpiperidine,
(±)-trans-4-[2-(N,N-diphenylamino)ethyl]-3-(2-methoxy-1-ethoxy)-N-pentylpiperidine, or
(±)-7-pentyl-10-(2-[4-chlorophenoxy]ethyl)-1,4-dioxa-7-aza-spiro[4,5]decane or a pharmaceutically-acceptable addition salt thereof;
a pharmaceutical composition comprising an effective amount of a compound as any above or a pharmaceutically-acceptable addition salt thereof, together with at least one pharmaceutically-acceptable carrier or diluent;
a process for the preparation of a compound as any above, comprising the step of
a) reacting a quinuclidinium salt of formula

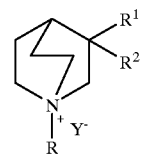

wherein R, R[1] and R[2] is as defined above and Y is a counter ion, with a compound of the formula HX—(CH$_2$)$_m$—Ar or a reactive derivative thereof, wherein X, m and Ar is as defined above, and thereafter optionally forming a pharmaceutically acceptable salt thereof, or b) reacting a compound of formula

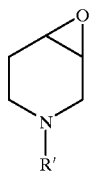

wherein R¹ is as defined for R above, or a protecting group, with a compound of formula HX—(CH$_2$)$_m$—Ar or a reactive derivative thereof, wherein X, m and Ar is as defined above, and thereafter optionally
  i) replacing a protective group with a group R using conventional methods, and/or
  ii) converting a compound obtained to another compound of the invention using conventional methods, and/or
  iii) forming a pharmaceutically acceptable salt thereof;
the use of a compound as any above for the manufacture of a medicament for the treatment of a disorder, which is responsive to the partial or complete blockade of calcium channels and/or sodium channels of the central nervous system, of a living animal body, including a human;
the use of a compound as any above for the manufacture of a medicament for the treatment of stroke, anoxia, ischemia, migraine, psychosis, or epilepsy or any other convulsive disorder, of a living animal body, including a human;
the use of a compound as any above for the manufacture of a medicament for the treatment of the degenerative changes connected with stroke, anoxia, ischemia, migraine, psychosis, or epilepsy or any other convulsive disorder, of a living animal body, including a human;
a method of treating a disorder or disease of a living animal body, including a human, which disorder or disease is responsive to the partial or complete blockade of calcium channels and/or sodium channel of the central nervous system comprising the step of administering to such a living animal body, including a human, in need thereof a therapeutically effective amount of a compound having the formula

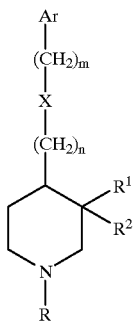

any of its enantiomers or any mixture thereof, or a pharmaceutically-acceptable addition salt thereof, wherein
  X is O, S, or NR³, wherein R³ is hydrogen, alkyl, or aryl which may be substituted one or more times with substitutents selected from the group consisting of alkyl, alkoxy, halogen, amino, nitro, cyano, trifluoromethyl, aryl, arylalkyl, aryloxy and arylalkyloxy;
  m is 0,1, or 2;
  n is 0,1, or 2;
  R is cycloalkyl, cycloalkylalky, (aryl)$_p$-alkyl, (aryl)$_p$-alkenyl, or (aryl)$_p$-alkynyl, wherein the aryl group may be substituted one or more times with substitutents selected from the group consisting of alkyl, alkoxy, halogen, amino, nitro, cyano and trifluoromethyl, and p is 0, or 1;
  one of R¹ and R² is —O—Z, or —S—Z, wherein Z is hydrogen; alkyl; alkenyl; alkynyl; cycloalkyl; cycloalkylalkyl; arylalkyl, arylalkenyl, arylalkenyl, or aryl-CO—, wherein the aryl groups may be substituted one or more times with substitutents selected from the group consisting of alkyl, alkoxy, halogen, amino, nitro, cyano and trifluoromethyl; or Z is —(CH$_2$)$_o$—CO—R⁶, —(CH$_2$)$_o$—COOR⁶, —(CH$_2$)$_o$—CONR⁶R⁷, or —(CH$_2$)$_o$—Het, wherein o is 0, 1, 2, 3, 4, or 5 and R⁶ and R⁷ each independently are hydrogen, or alkyl, and Het is a five or six membered monocyclic heterocyclic ring; or Z is —(CH$_2$)$_o$—WR⁴, or

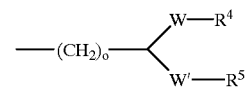

wherein o is 0, 1, 2, 3, 4, or 5, W and W' each independently are O, or S, and R⁴ and R⁵ each independently are hydrogen, or alkyl, or wherein R⁴ and R⁵ together is —(CH$_2$)$_q$—, wherein q is 2, or 3; and the other of R¹ and R² is hydrogen, alkoxy, or alkoxyalkoxy; or R¹ and R² together form a chain —W—(CH$_2$)$_q$—W'—, wherein W and W' each independently are O, or S and q is 2, or 3; and
  Ar is aryl which may be substituted one or more times with substitutents selected from the group consisting of alkyl, alkoxy, halogen, amino, nitro, cyano, trifluoromethyl, aryl, arylalkyl, aryloxy, and arylalkyloxy;
with the proviso that said compound is not trans-3-hydroxy-4-(3,4-dimethylphenoxy)-1-methyl-piperidine-hydrochloride,
trans-3-hydroxy-4-phenylthio-1-methyl-piperidine,
cis/trans-3-methoxy-4-(3,4-dimethylphenoxy)-1-methyl-piperidine,
trans-3-hydroxy-4-(3,4dimethylphenoxy)-1-propargyl-piperidine,
trans-4-hydroxy-3-(3,4-dimethylphenoxy)-1-methyl-piperidine,
trans-3-hydroxy-4-(2-bromo-4-methoxyphenoxy)-1-methyl-piperidine,
cis/trans-3-hydroxy-4-(2,3-dimethylphenoxy)-1-methyl-piperidine,
cis-3-hydroxy-4-(3,4-dimethylphenoxy)-1-methyl-piperidine,
cis/trans-3-hydroxy-4-(1-naphthyloxy)-1-methyl-piperidine,
cis/trans-3-hydroxy-4-(m-chlorophenoxy)-1-methyl-piperidine,
cis/trans-3-hydroxy-4-(5,6,7,8-tetrahydro-1-naphthyloxy)-1-methyl-piperidine,
cis/trans-3-hydroxy-4-(p-fluorophenoxy)-1-methyl-piperidine,
trans-3-acetoxy-4-(3,4-dimethylphenoxy)-1-methyl-piperidine,
trans-3-hydroxy-4-(p-trifluoromethylphenoxy)-1-methyl-piperidine,
cis/trans-3-methoxy-4-(2,3-dimethylphenoxy)-1-methyl-piperidine, 1-phenylmethyl-3-methoxy-4-phenylaminopiperidine, or a compound having the formula

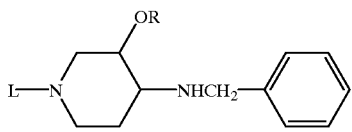

wherein R represents hydrogen or methyl and L is selected from —CH$_2$—Ph, —(CH$_2$)$_3$—CH(4F—Ph)$_2$, or ethyl, with Ph being phenyl; and a method as above wherein the disorder or disease is stroke, anoxia, ischemia, migraine, psychosis, or epilepsy or any other convulsive disorder or the degenerative changes connected with the above disorders.

Halogen is fluorine, chlorine, bromine, or iodine.

Alkyl means a straight chain or branched chain of from one to six carbon atoms, including but not limited to, methyl, ethyl, propyl, isopropyl, butyl, isobutyl, t-butyl, pentyl and hexyl; methyl, ethyl, propyl and isopropyl are preferred groups.

Cycloalkyl means cyclic alkyl of from three to seven carbon atoms, including but not limited to cyclopropyl, cyclobutyl, cyclopentyl, or cyclohexyl.

Alkenyl means a straight or branched chain of from two to six carbon atoms, containing one double bond, including but not limited to ethenyl, 1 or 2-propenyl, 1, 2, or 3-butenyl.

Alkynyl means a means a straight or branched chain of from two to six carbon atoms, containing one triple bond, including but not limited to ethynyl, 1, or 2-propynyl, 1, 2, or 3-butynyl.

Cycloalkylalky means cycloalkyl as above and alkyl as above, meaning for example, cyclopropylmethyl.

Alkoxy is O-alkyl, wherein alkyl is as defined above.

Aryl means phenyl, naphthyl, or tetrahydronaphthyl.

Amino means —NH$_2$, —NH(alkyl), or —N(alkyl)$_2$.

A 5- or 6-membered heterocyclic monocyclic group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, and 4-pyrazolyl.

Examples of pharmaceutically-acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate for example.

Other acids such as oxalic acid, while not in themselves pharmaceutically acceptable may be useful in the preparation of salts useful as intermediates in obtaining compounds of the invention and their pharmaceutically acceptable acid addition salts.

Such salts are formed by procedures well known in the art.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l- (tartrates, mandelates, or camphorsulphonate) salts for example. The compounds of the instant invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Pure enantiomers can also be obtained by the use of optically active starting materials.

Additional methods for the resolvation of optical isomers, known to those skilled in the art may be used, and will be apparent to a person skilled in the art. Such methods include those discussed by J. Jaques, A. Collet, and S. Wilen in "Enantiomers, Racemates, and Resolutions", John Wiley and Sons, New York (1981).

In one embodiment the compounds of the invention are prepared as described in the following reaction scheme. The reaction can be carried out as a one-pot reaction:

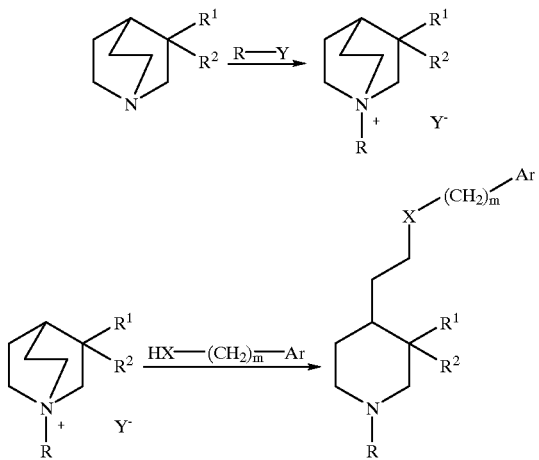

The leaving group Y may be a halide, such as bromide, chloride or iodide or a sulfonyloxy group such as methylsulphonyloxy, benzenesulphonyloxy, or p-toluenesulphonyloxy. The quarternization of the quinuclidine ring may be carried out in conventional manner, without the use of solvent, or in an organic solvent, for example alcohols, such as methanol, ethanol, isopropanol and phenol, ethers such as diisopropylether, tetrahydrofuran or dioxan, amides such as dimethylformamide, or in halogenated-, or aromatic- or aliphatic hydrocarbons such as chloroform, dichlormethan, benzene, toluene, xylene and hexane. Preferably the reaction is carried out without the use of solvent. Temperatures between 20 and 200° C. is appropriate for the reaction.

The ring opening reaction may be carried out without the use of solvent or in an inert solvent with high boiling point. Preferably the reaction is carried out without the use of solvent.

Preferably the ring opening reaction is carried out in the presence of an organic or inorganic base, for example hydroxides, such as NaOH, KOH, CsOH, or RbOH or carbonates, such as $Na_2CO_3$, $K_2CO_3$, $Cs_2CO_3$, $Rb_2CO_3$, $NaHCO_3$, $KHCO_3$, and $CsHCO_3$. Preferably the reaction takes place in the presence of $Cs_2CO_3$. Temperatures between 100 and 250° C., preferably between 150 and 200° C., are appropriate for the reaction. Suitably the reaction is carried out in an inert atmosphere.

The products of the reaction described herein are isolated by conventional means such as extraction, crystallisation, distillation, chromatography and the like.

Starting materials for the processes described herein are known or can be prepared by known processes from commercially available chemicals.

Biology

In neurons, calcium enters the cytoplasma from the extracellular milieu through voltage-sensitive calcium-channels. Six classes of physiologically distinct calcium channels have been identified to date, namely the T, L, N, P, Q, and R-type channels. Although different channel types appear to act different in neurons, the most consistent generalization is that N-type channels are involved in mediating the release of neurotransmitters.

One approach to the study of mechanism and properties of voltage-sensitive calcium channels in the central nervous system, is by measurements of $^{45}Ca$-uptake/influx into nerve terminals (synaptosomes).

In chick cortical synaptosomes, calcium entry induced by potassium depolarization has been shown to be inhibited potently and almost totally by N-type channel blockers, i.e., the ω-conotoxins GVIA and MVIIA suggesting that this tissue preparation has a high percentage of N-type channels. L-type channel blockers are very weak inhibitors of $^{45}Ca$-uptake in chick synaptosomes.

Tissue preparation: Tissue preparations are performed at 0–4° C. unless otherwise indicated. A chick is decapitated and the cerebral cortex removed and gently homogenized in 20 ml of ice-cold 0.32 M sucrose using a motor driven teflon pestle in a glass homogenizing vessel. The homogenate is centrifuged at 1,000×g for 10 min. The resulting supernatant is recentrifuged at 17,000×g for 20 min. The pellet is resuspended in 0.32 M sucrose (2 ml per g of original tissue) with a teflon pestle and left on ice for 60 min. After centrifugation for 10 min at 27,000×g the pellet is resuspended in choline Tris-buffer (136 mM choline chloride, 4 mM KCl, 0.32 mM $CaCl_2$, 1.2 mM $MgCl_2$, 20 mM Tris-HCl, 12 mM glucose, pH 7.4) (27 ml per g of original tissue), and used for the uptake assay.

Assay: 250 μl of tissue suspension are added to 10 μl of test solution. The samples are preincubated for 30 min on ice followed by 6 min at 37° C. on a water bath. At the end of the incubation period, a 130 μl aliquot of this synaptosomal suspension is injected into 75 μl of resting choline Tris-buffer ( 4 mM $K^+$) or depolarization choline Tris-buffer (30 mM $K^+$) containing approximately 0.3 μCi $^{45}Ca^{2+}$. The influx occurs for 10 sec and is then stopped by rapid filtration of the samples over glass fibre filters (previously soaked in 0.1% PEI and dried) using a Skatron cell harvester. The filters are washed with 3 ml of ice-cold $Ca^{2+}$-free Tris-buffer containing 7 mM EGTA. The filters are dried and the amount of radioactivity on the filters is determined by conventional liquid scintillation counting. Specific $^{45}Ca$-uptake is uptake in depolarizing choline Tris-buffer (30 mM $K^+$) minus uptake in resting choline Tris-buffer (4 mM $K^+$).

The test value is given as $IC_{50}$, the concentration (μM) of test substance which inhibits the specific uptake of $^{45}Ca$ by 50%.

Test values for certain compounds of the invention appear from the table below:

TABLE 1

| Compound | $IC_{50}(\mu M)$ |
|---|---|
| (±)-trans-4-[2-(3,4-Dichlorophenoxy)-ethyl]-3-methoxy-N-pentylpiperidinium | 0.7 |
| (±)-cis-4-[2-(2,3-Dimethylphenoxy)-ethyl]-3-methoxy-N-pentylpiperidine | 0.9 |
| (±)-cis-4-[2-(3,4-Dichlorophenoxy)-ethyl]-3-(2-methoxy)-ethoxy-N-pentylpiperidine | 0.3 |
| (±)-trans-4-[2-(3,4-Dichlorophenoxy)-ethyl]-3-(2-methoxy)-ethoxy-N-pentylpiperidine | 0.4 |
| (±)-trans-4-[2-(3,4-Dichlorophenoxy)-ethyl]-3-acetoxy-N-pentylpiperidine | 0.5 |
| (±)-trans-4-[2-(3-isopropoxyphenoxy) ethyl]-3-(2-methoxy-1-ethoxy)-N-pentylpiperidine | 1.1 |
| (±)-trans-4-[4-phenoxyphenoxy]-3-(2-methoxy-1-ethoxy)-N-pentylpiperidine | 0.62 |
| (±)-trans-4-[2-(N,N-diphenylamino)ethyl]-3-methoxy-N-pentylpiperidine | 1.3 |
| (±)-cis-4-[2-(N,N-diphenylamino)ethyl]-3-methoxy-N-pentylpiperidine | 1.10 |
| (±)-cis-4-[2-(2-phenylphenoxy)ethyl]-3-methoxy-N-pentylpiperidine | 1.0 |
| (±)-trans-4-[(4-chlorobenzyl)thio]-3-(2-methoxy-1-ethoxy)-N-pentylpiperidin | 1.0 |
| (±)-cis-4-[2-(2-benzylphenoxy)ethyl]-3-methoxy-N-pentylpiperidine | 0.9 |
| (±)-trans-4-[2-(2-benzylphenoxy)ethyl]-3-methoxy-N-pentylpiperidine | 0.6 |
| (±)-trans-4-[(2-benzyloxyphenoxy)]-3-(2-methoxy-1-ethoxy)-N-pentylpiperidine | 0.9 |
| (±)-trans-4-[2-(N,N-diphenylamino)ethyl]-3-(2-methoxy-1-ethoxy)-N-pentylpiperidine | 0.5 |

Generally the compounds of the present invention block 50% of the calcium influx through N type calcium channels in the low micromolar range.

Furthermore, it has been found (electrophysiological studies using the patch-clamp technique as described by Hamill et al., Pflügers Arch. 391, 85–100 (1981)), that compounds of the invention block the N-type calcium channels as well as sodium channels the low micromolar range (1–10 μM).

The compounds of the invention are therefore useful in the treatment of disorders or diseases responsive to the blockade of calcium channels, such as anoxia, cerebral ischemia or stroke and migraine.

Pharmaceutical Compositions

While it is possible that, for use in therapy, a compound of the invention may be administered as the raw chemical, then it is preferable to present the active ingredient as a pharmaceutical formulation.

The invention thus further provides a pharmaceutical formulation comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing one (1) milligram of active ingredient or, more broadly, 0.01 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting vax, cocoa buffer, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting vax, such as a mixture of fatty acid glycerides or cocoa buffer, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water propylene glycol solutions. For example, parenteral injection liquid preparations can be formulated in solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasel cavity by conventional means, for example with a dropper, pipette or spray. The formulations may be provided in single or multidose form. In the latter case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of the invention may be administered to a subject, e.g., a living animal body, in need of alleviation, treatment, or amelioration of a disorder which is responsive to the activity or influence of the compounds of the present invention including responsive to the Ca and/or Na channel blocking properties of the compounds of the invention. Due to their calcium channel blocking activity, the compounds of the invention are useful as neuroprotective and antiischemic agents for the treatment of cerebral disorders (e.g. disorders resulting from an ischemic attack, cardiac or respiratory arrest, cerebral thrombosis or embolism), cerebral senility, multiinfarct dementia, senile dementia (e.g. Alzheimer's disease), Pick's disease, olivopontocerebellar atrophy, neurodegenerative disorders (e.g. Huntington's disease and amyotropic lateral sclerosis), brain or spinal trauma, prevention of neuronal pain caused by convulsions, treatment of cancer, neurological disorders due to AIDS, diabetic retinopathy and retinopathy due to glaucoma.

The compounds of the invention are preferably administered in the form of an acid addition salt thereof, concurrently, simultaneously, or together with a pharmaceutically-acceptable carrier or diluent, especially and preferably in the form of a pharmaceutical composition thereof, whether oral, rectal, or parenteral (including subcutaneous) route, in an effective amount. Suitable dosage ranges are 1–500 milligrams daily, preferably 1–100 milligrams daily, and especially 1–30 milligrams daily, depending as usual upon the exact mode of administration, form in which administered, the indication toward which the administration is directed, the subject involved and the body weight of the subject involved, and the preferences and experience of the physician or veterinarian in charge.

The following examples will illustrate the invention further; however they are not to be construed as limiting.

EXAMPLE 1

(±)-3-Hydroxy-1-pentylquinuclidinium bromide. A mixture of (±)-3-hydroxyquinuclidine (25 g, 196 mmol) and 1-bromopentane (32.6 g, 216 mmol) was refluxed in ethanol (200 ml) for 2 h. Trituration with petrol ether gave the title compound as soft white crystals. Yield 54 g, 99%.

EXAMPLE 2

(±)-Methoxy-1-pentylquinuclidinium bromide. To a suspension of (±)-3-hydroxy-1-pentylquinuclidinium bromide (20 g, 72 mmol) in dry 1,2-dimethoxyethane (150 ml) at 0° C., under nitrogen, was added sodium hydride (3.48 g, 60% in mineral oil, 86.8 mmol) and then iodomethane (11.3 ml, 181 mmol). The temperature was allowed to rise to room temperature overnight. Water (200 ml) was added and the mixture was extracted with 6×100 ml dichloromethane. Drying and evaporation gave an oily residue which, after trituration with petrol ether, gave the title compound as a crystalline solid. Yield 23.9 g (That the yield was more than 100% is explained by the fact that there is a mixture of bromide and iodide as counter ions.).

In a similar way (±)-3-ethoxy-1-pentylquinuclidinium bromide, (±)-3-cyclohexylmethoxy-1-pentylquinuclidinium bromide, (±)-3-(2-methoxyethoxy)-1-pentylquinuclidinium bromide, and (±)-3-(3-methylbut-2-en-1-oxy)-1-pentylquinuclidinium bromide was prepared.

EXAMPLE 3

(±)-trans-4-[2-(3,4-Dichlorophenoxy)-ethyl]-3-methoxy-N-pentylpiperidinium oxalate and (±)-cis-4-[2-(3,4-dichlorophenoxy)-ethyl]-3-methoxy-N-pentylpiperidinium oxalate. A mixture of (±)-3-methoxy-1-pentylquinuclidinium bromide (4.00 g, 13.7 mmol), 3,4-dichlorophenol (3.36 g, 20.6 mmol), and cesium carbonate (4.46 g, 13.7 mmol) was heated to 170° C. under nitrogen for 16 h. The crude product was dissolved in a mixture of ether and water and the phases were separated. The aqueous layer was extracted once more with ether. The combined organic phases were extracted twice with 1 M aqueous hydrochloric acid. The acidic phases were washed with ether and was then made basic by the addition of 4 M aqueous sodium hydroxide. This basic phase was now extracted twice with ether which, after treatment with activated charcoal, was dried and evaporated. The trans isomer was separated from the cis isomer by chromatography on silica gel with a 9 to 1 mixture of dichloromethane and ethanol with the trans isomer eluting as the slower fraction. The pure trans isomer was dissolved in ether and precipitated as the oxalate by the addition of an excess of a saturated solution of oxalic acid in ether. Yield 1.1 g, 2.4 mmol 18%, mp 148–151° C. The pure cis isomer was dissolved in ether and precipitated as the oxalate by the addition of an excess of a saturated solution of oxalic acid in ether. Yield 1.2 g, 2.7 mmol 19%, mp 144–147° C.

In a similar way the following compounds were prepared by suitable combinations of the above quinuclidinium salts and substituted phenols, anilines, or thiophenols:

(±)-trans-4-[2-(3-Chlorophenoxy)-ethyl]-3-hydroxy-N-pentylpiperidinium chloride mp 150–153° C.
(±)-cis-4-[2-(3-Chlorophenoxy)-ethyl]-3-hydroxy-N-pentylpiperidine mp 58–59° C.
(±)-trans-4-[2-(4-Chlorophenoxy)-ethyl]-3-hydroxy-N-pentylpiperidine mp 66–67° C.

(±)-cis-4-[2-(4-Chlorophenoxy)-ethyl]-3-hydroxy-N-pentylpiperidine. mp 65–70° C.
(±)-cis-4-[2-(3,4-Dichlorophenoxy)-ethyl]-3-hydroxy-N-pentylpiperidine mp 75–77° C.
(±)-trans-4-[2-(3,4-Dichlorophenoxy)-ethyl]-3-hydroxy-N-pentylpiperidine hydrochloride. mp 170–177° C.
(±)-trans-4-[2-(3-Chlorophenoxy)-ethyl]-3-methoxy-N-pentylpiperidine oxalic acid salt mp 172–179° C.
(±)-cis-4-[2-(3-Chlorophenoxy)-ethyl]-3-methoxy-N-pentylpiperidine oxalic acid salt mp 153–156° C.
(±)-cis-4-[2-(4-Chlorophenoxy)-ethyl]-3-methoxy-N-pentylpipenidine oxalic acid salt mp 120–121° C.
(±)-trans-4-[2-(4-Chlorophenoxy)-ethyl]-3-methoxy-N-pentylpiperidine oxalic acid salt mp 155–156° C.
(±)-cis-4-[2-(3-Methoxyphenoxy)-ethyl]-3-methoxy-N-pentylpiperidine oxalic acid salt mp 141–143° C.
(±)-trans-4-[2-(3-Methoxyphenoxy)-ethyl]-3-methoxy-N-pentylpiperidine oxalic acid salt mp 143–144° C.
(±)-cis-4-[2-(3-Chlorophenylthio)-ethyl]-3-methoxy-N-pentylpiperidine oxalic acid salt mp 156–158° C.
(±)-trans-4-[2-(3-Chlorophenylthio)-ethyl]-3-methoxy-N-pentylpipenidine oxalic acid salt mp 175–176° C.
(±)-cis-4-[2-(3-Trifluoromethylphenoxy)-ethyl]-3-methoxy-N-pentylpiperidine oxalic acid salt mp 163–168° C.
(±)-trans-4-[2-(3-Trifluoromethylphenoxy)-ethyl]-3-methoxy-N-pentylpiperidine oxalic acid salt mp 164–170° C.
(±)-cis-4-[2-(4-Phenylphenoxy)-ethyl]-3-methoxy-N-pentylpiperidine oxalic acid salt mp 97–105° C.
(±)-trans-4-[2-(4-Phenylphenoxy)-ethyl]-3-methoxy-N-pentylpiperidine oxalic acid salt mp 181–184° C.
(±)-cis-4-[2-(2,3-Dimethylphenoxy)-ethyl]-3-methoxy-N-pentylpiperidine oxalic acid salt mp 138–139° C.
(±)-trans-4-[2-(2,3-Dimethylphenoxy)-ethyl]-3-methoxy-N-pentylpiperidine oxalic acid salt mp 156–158° C.
(±)cis-4-[2-(4-Bromophenoxy)-ethyl]-3-methoxy-N-pentylpiperidine oxalic acid salt mp 128–132° C.
(±)-trans-4-[2-(4-Bromophenoxy)-ethyl]-3-methoxy-N-pentylpiperidine oxalic acid salt mp 141–146° C.
(±)-cis-4-[2-(3,4-Dichlorophenoxy)-ethyl]-3-(2-methoxy)-ethoxy-N-pentylpiperidine oxalic acid salt. mp 145–147° C.
(±)-trans-4-[2-(3,4-Dichlorophenoxy)-ethyl]-3-(2-methoxy)-ethoxy-N-pentylpiperidine oxalic acid salt. mp 156–158° C.
(±)-trans-4-[2-(3,4-Dichlorophenoxy)-ethyl]-3-acetoxy-N-pentylpiperidine oxalic acid salt. mp 129–131° C.
(3R,4R)-4-[2-(3,4-Dichlorophenoxy)-ethyl]-3-methoxy-N-pentylpiperidine oxalic acid salt. mp 139.5–140.5° C.
(3R,4S)-4-[2-(3,4-Dichlorophenoxy)-ethyl]-3-methoxy-N-pentylpiperidine oxalic acid salt. mp 142.5–143.5° C.
(±)-cis-4-[2-(4-tert-butylphenoxy)-ethyl]-3-methoxy-N-pentylpiperidine oxalic acid salt mp 149–154° C.
(±)-trans-4-[2-(4-tert-butylphenoxy)-ethyl]-3-methoxy-N-pentylpipenidine oxalic acid salt mp 89–97° C.
(±)-cis-4-[2-(3-Chloro-5-methoxyphenoxy)-ethyl]-3-methoxy-N-pentylpiperidine oxalic acid salt mp 157–161° C.
(±)-trans-4-[2-(3-Chloro-5-methoxyphenoxy)-ethyl]-3-methoxy-N-pentylpiperidine oxalic acid salt mp 121–125° C.
(±)-cis-4-[2-(4-Phenoxyphenoxy)-ethyl]-3-methoxy-N-pentylpipeddine oxalic acid salt mp 136–140° C.
(±)-trans-4-[2-(4-Phenoxyphenoxy)-ethyl]-3-methoxy-N-pentylpiperidine oxalic acid salt mp 139–142° C.
(±)-cis-4-[2-(3-Isopropoxyphenoxy)-ethyl]-3-methoxy-N-pentylpiperidine oxalic acid salt mp 123–127° C.
(±)-trans-4-[2-(3-Isopropoxyphenoxy)-ethyl]-3-methoxy-N-pentylpiperidine oxalic acid salt mp 52–56° C.
(±)-cis-4-[2-(4-Nitrophenoxy)-ethyl]-3-methoxy-N-pentylpiperidine oxalic acid salt mp 123–126° C.
(±)-trans-4-[2-(4-Nitrophenoxy)-ethyl]-3-methoxy-N-pentylpiperidine oxalic acid salt mp 52–58° C.
(±)-cis-4-[2-(2-{5,6,7,8-Tetrahydronaphtoxy})-ethyl]-3-methoxy-N-pentylpiperidine oxalic acid salt mp 109–116° C.
(±)-trans-4-[2-(2-{5,6,7,8-Tetrahydronaphtoxy})-ethyl]-3-methoxy-N-pentylpiperidine oxalic acid salt mp 140–146° C.
(±)-cis-4-[2-(4-Chloro-3-methylphenoxy)-ethyl]-3-methoxy-N-pentylpiperidine oxalic acid salt mp 138–140° C.
(±)-trans-4-[2-(4-Chloro-3-methylphenoxy)-ethyl]-3-methoxy-N-pentylpipeidine oxalic acid salt mp 142–146° C.
(±)-cis-4-[2-(3,5-Dichlorophenoxy)-ethyl]-3-methoxy-N-pentylpiperidine oxalic acid salt mp 143–145° C.
(±)-trans-4-[2-(3,5-Dichlorophenoxy)-ethyl]-3-methoxy-N-pentylpiperidine oxalic acid salt mp 142–144° C.
(±)-cis-4-[2-(3,4-Dichlorophenoxy)-ethyl]-3-(3-methylbut-2-en-1-oxy)-N-pentylpiperidine oxalic acid salt mp 171–175° C.
(±)-trans-4-[2-(3,4-Dichlorophenoxy)-ethyl]-3-(3-methylbut-2-en-1-oxy)-N-pentylpiperidine oxalic acid salt mp 138–143° C.
(±)-cis-4-[2-(3,4-Dichlorophenoxy)-ethyl]-3-ethoxy-N-pentylpiperidine oxalic acid salt mp 135–143° C.
(±)-trans-4-[2-(3,4-Dichlorophenoxy)-ethyl]-3-ethoxy-N-pentylpiperidine oxalic acid salt mp 170–175° C.
(±)-cis-4-[2-(3,4-Dichlorophenoxy)-ethyl]-3-cyclohexylmethoxy-N-pentylpiperidine oxalic acid salt mp 119–120° C.
(±)-trans-4-[2-(3,4-Dichlorophenoxy)-ethyl]-3-cyclohexylmethoxy-N-pentylpiperidine oxalic acid salt mp 78–82° C.
(±)-trans-4-[2-(3-isopropoxyphenoxy) ethyl]-3-(2-methoxy-1-ethoxy)-N-pentylpiperidine oxalate M.p. 75–78° C.
(±)-trans-4-[2-(N,N-diphenylamino)ethyl]-3-methoxy-N-pentylpiperidine oxalate M.p. 119.6–124.1° C.
(±)-cis-4-[2-(N,N-diphenylamino)ethyl-3-methoxy-N-pentylpiperidine oxalate M.p. 147–152° C.
(±)-cis-4-[2-(2-phenylphenoxy)ethyl]-3-methoxy-N-pentylpiperidine oxalate M.p. 166.3–172.2° C.
(±)-cis-4-[2-(2-benzylphenoxy)ethyl]-3-methoxy-N-pentylpiperidine oxalate M.p. 124–132° C.
(±)-trans-4-[2-(2-benzylphenoxy)ethyl]-3-methoxy-N-pentylpiperidine oxalate M.p. 136–143° C.
(±)-trans-4-[2-(N,N-diphenylamino)ethyl]-3-(2-methoxy-1-ethoxy)-N-pentylpiperidine, olie

EXAMPLE 4

N-tert-Butoxycarbonyl-3,4-epoxypiperidine. A mixture of N-tert-butoxycarbonyl-1,2,3,6-tetrahydropyrdine (23.6 g, 129 mmol), and m-chloroperbenzoic acid (46 g, 193 mmol) in dichloromethane (600 ml) at 0° C. was stirred and allowed to reach room temperature overnight. Washing with 5% aqueous sodium sulfite (700 ml), 3% aqueous sodium hydrogen carbonate (700 ml), 1 M aqueous sodium hydroxide (700 ml), and, finally, water (700 ml). Drying and evaporation was followed by purification by column chromatography on silica gel with 3% ethanol in dichloromethane. The title compound was obtained as a colorless oil. Yield 8.4 g, 33%.

EXAMPLE 5

(±)-trans-N-tert-Butoxycarbonyl-3-hydroxy-4-(4-phanoxyphenoxy)-piperidine. A mixture of 4-phenoxyphenol (0.93 g, 5.0 mmol), N-tert-butoxycarbonyl-3,4-epoxypiperidine (1.0 g, 5.0 mmol), and potassium carbonate (0.69 g, 5.0 mmol) in ethanol (20 ml) was refluxed for 3 h. Water was added and the product was extracted with ether (2×50 ml). Drying and evaporation gave the title compound as an oil.

EXAMPLE 6

(±)-trans-N-tert-Butoxycarbonyl-4-(4-phenoxyphenoxy)-3-(2-methoxy-1-ethoxy)piperidine. To a solution of (±)-trans-N-tert-butoxycarbonyl-3-hydroxy-4-(4-phenoxyphenoxy)-piperidine (1.47 g, 3.8 mmol) in dry DMF (30 ml) was added sodium hydride (300 mg 60% suspension in mineral oil, 4.2 mmol). After 1 h, 2-bromoethyl methyl ether (1.7 g, 7.6 mmol) was added. After 6 days water was added and the product was extracted with ethyl acetate (2×30 ml). After drying and evaporation the crude product was obtained as an oil.

EXAMPLE 7

(±)-trans-4-(4-phenoxyphenoxy)-3-(2-methoxy-1-ethoxy)piperidine trifluoroacetic acid salt. To a solution of (±)-trans-N-tert-butoxycarbonyl-4-(4-phenoxyphenoxy)-3-(2-methoxy-1-ethoxy)piperidine (2.1 g, 4.7 mmol) in dry dichloromethane (20 ml) and trifluoroacetic acid (1.5 ml) was added. After 2 h the volatiles were evaporated. The residue was triturated with petroleum ether to leave the title compound as an oil. Yield 2.2 g 100%.

EXAMPLE 8

(±)-trans-N-Pentyl-4-(4-phenoxyphenoxy)-3-(2-methoxy-1-ethoxy)piperidine oxalic acid salt. To a solution of (±)-trans-4-(4-phenoxyphenoxy)-3-(2-methoxy-1-ethoxy)piperidine (0.50 g, 1.5 mmol) and 1-bromopentane (242 mg, 1.6 mmol) in DMF (10 ml) was added potassium carbonate (300 mg, 2.2 mmol) and the mixture was stirred at 100° C. for 3 h. Water (50 ml) was added and the product was extracted with ethyl acetate (3×20 ml). Drying over magnesium sulfate and evaporation of the solvent was followed by column chromatography on silica gel with 4% ethanol in dichloromethane. The title compound was obtained by dissolving the product in ether and adding a saturated solution of oxalic acid in ether. mp 122–124° C.

In a similar way, following the sequence of ring opening of N-tert-butoxycarbonyl-3,4-epoxypiperidine with a suitable nucleophile and alkylation of the hydroxy group, deprotection, and N-alkylation, the following compounds were prepared:

(±)-trans-4-[(4-chlorobenzyl)thio]-3-(2-methoxy-1-ethoxy)-N-pentylpiperidine oxalate. mp 109–1 10° C.
(±)-trans-4-(2-benzyloxyphenoxy)-3-(2-methoxy-1-ethoxy)-N-pentylpiperidine oxalate. mp 83–86° C.

EXAMPLE 9

3,3-Dimethoxyquinuclidine. A mixture of 3-quinuclidinone hydrochloride (5.00 g, 30.9 mmol), 2,2 dimethoxypropane (50 ml), and methanesulfonic acid (0.1 ml) was refluxed for 8 h. The reaction mixture was poured in pH 7.4 phosphate buffer (20 ml) and washed 4 times with ethyl acetate. The aqueous phase was made basic by the addition of 4 M NaOH. Extraction with 3 portions of ethyl acetate gave, after drying and evaporation the title compound as a colorless oil. Yield 4.00 g (75%).

EXAMPLE 10

3-Quinuclidinone ethyleneketal. A mixture of 3-quinuclidinone hydrochloride (5 g, 31 mmol) and ethylene glycol (20 ml) was heated under nitrogen at 200° C. (bath temperature) for 2 h. After cooling, the reaction mixture was poured in an excess of 1 M aqueous sodium hydroxide. Extraction with three portions of ethyl acetate was followed by drying over magnesium sulfate, and evaporation of the solvent to yield the product (5.2 g, 31 mmol, 100%) as a colorless oil.

EXAMPLE 11

3-Quinuclidinone trimethylenethioketal. A mixture of 3-quinuclidinone hydrochloride (10 g, 62 mmol), 1,3-propanedithiol (13.4 g, 124 mmol), acetic acid (40 ml), and methanesulfonic acid (2 ml) was refluxed overnight. Most of the acetic acid was evaporated, 200 ml of water was added, and the solution was washed twice with ether. The pH of the solution was adjusted to basic by the addition of 1 M aqueous sodium hydroxide and the product was extracted with two portions of ethyl acetate. Drying over magnesium sulfate and evaporation of the solvent gave the title compound (13.3 g, 61.9 mmol, 100%) as a colorless solid 71–72° C.

EXAMPLE 12

3,3-Dimethoxy-1-pentylquinuclidinium bromide. A mixture of 3,3-dimethoxyquinuclidine (1.71 g, 10 mmol) and 1-bromopentane (1.51g, 10 mmol) was heated at 110° C. for 15 min. Yield 3.22 g, 100%.

In a similar way N-pentyl-3-quinuclidinone ethyleneketal bromide, and N-pentyl-3-quinuclidinone trimethylenethioketal bromide was prepared.

EXAMPLE 13

(±)-4-[2-3,4-Dichlorophenoxy)ethyl]-3,3-dimethoxy-N-pentylpiperidine oxalic acid salt. A mixture of 3,3-dimethoxy-1-pentylquinuclidinium bromide (3.22 g, 10.0 mmol), 3,4-dichlorophenol (2.44 g, 15.0 mmol), and cesium carbonate (3.26 g, 10.0 mmol) was heated to 170° C. under nitrogen for 15 h. The crude product was dissolved in a mixture of ether and 1 M aqueous sodium hydroxide and the phases were separated. After treatment with activated charcoal the ethereal phase was dried and the product was precipitated as the oxalate by the addition of an excess of a saturated solution of oxalic acid in ether. mp 160–161° C.

In a similar way the following compounds were prepared by suitable combinations of the above quinuclidinium salts and substituted phenols or anilines:

(±)-7-Pentyl-10-(2-[3,4-dichlorophenoxy]ethyl)-1,4-dioxa-7-aza-spiro[4,5]decane oxalic acid salt. mp 84–86° C.
(±)-4-[2-(3-Chlorophenylamino)-ethyl]-3,3-dimethoxy-N-pentylpiperidine oxalic acid salt. mp 138–139° C.
(±)-7-Pentyl-10-(2-[3-chlorophenoxy]ethyl)-1,4-dioxa-7-aza-spiro[4,5]decane oxalic acid salt. mp 175–177° C.
(±)-7-Pentyl-10-(2-[3-chlorophenylamino]ethyl)-1,4-dioxa-7-aza-spiro[4,5]decane oxalic acid salt. mp 134–136° C.
(±)-8-Pentyl-1 1-(2-[3,4-dichlorophenoxy]ethyl)-1,5-dithio-8-aza-spiro[5,5]undecane oxalic acid salt. mp 138–140° C.
(±)-7-Pentyl-10-(2-[4-chlorophenoxy]ethyl)-1,4-dioxa-7-azaspiro[4,5]decane oxalic acid salt. mp 182–188° C.
(±)-7-Methyl-10-(2-[3-chlorophenoxy]ethyl)-1,4-dioxa-7-azaspiro[4,5]decane oxalic acid salt. mp 161–163° C.

We claim:
1. A compound having the formula

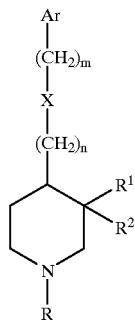

any of its enantiomers or any mixture thereof, or a pharmaceutically-acceptable addition salt thereof, wherein X is O, S, or $NR^3$, wherein $R^3$ is hydrogen, alkyl, or aryl which may be substituted one or more times with substitutents selected from the group consisting of alkyl, alkoxy, halogen, amino, nitro, cyano, trifluoromethyl, aryl, arylalkyl, aryloxy and arylalkyloxy;

m is 0,1, or 2;

n is 0,1, or 2;

R is cycloalkyl, cycloalkylalky, $(aryl)_p$-alkyl, $(aryl)_p$-alkenyl, or $(aryl)_p$-alkynyl, wherein the aryl group may be substituted one or more times with substitutents selected from the group consisting of alkyl, alkoxy, halogen, amino, nitro, cyano and trifluoromethyl, and p is 0, or 1;

one of $R^1$ and $R^2$ is —O—Z, or —S—Z, wherein Z is hydrogen; alkyl; alkenyl; alkynyl; cycloalkyl; cycloalkylalky; arylalkyl, arylalkenyl, arylalkynyl, or aryl-CO—, wherein the aryl groups may be substituted one or more times with substitutents selected from the group consisting of alkyl, alkoxy, halogen, amino, nitro, cyano and trifluoromethyl; or Z is —$(CH_2)_o$—CO—$R^6$, —$(CH_2)_o$—$COOR^6$, —$(CH_2)_o$—$CONR^6R^7$, or —$(CH_2)_o$—Het, wherein o is 0, 1, 2, 3, 4, or 5 and $R^6$ and $R^7$ each independently are hydrogen, or alkyl, and Het is a five or six membered monocyclic heterocyclic ring; or Z is —$(CH_2)_o$—$WR^4$, or

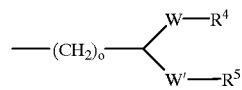

wherein o is 0, 1, 2, 3, 4, or 5, W and W' each independently are O, or S, and $R^4$ and $R^5$ each independently are hydrogen, or alkyl, or wherein $R^4$ and $R^5$ together is —$(CH_2)_q$—, wherein q is 2, or 3; and the other of $R^1$ and $R^2$ is hydrogen, alkoxy, or alkoxyalkoxy; or $R^1$ and $R^2$ together form a chain —W—$(CH_2)_q$—W'—, wherein W and W' each independently are O, or S and q is 2, or 3; and Ar is aryl which may be substituted one or more times with substitutents selected from the group consisting of alkyl, alkoxy, halogen, amino, nitro, cyano, trifluoromethyl, aryl, arylalkyl, aryloxy, and arylalkyloxy;

with the proviso that when m and n are both zero, one of $R^1$, $R^2$ is alkoxyalkoxy and R is an alkylene chain with at least 2 carbon atoms; and with the proviso that said compound is not trans-3-hydroxy-4-(3,4-dimethylphenoxy)-1-methyl-piperidine-hydrochloride,
trans-3-hydroxy-4-phenylthio-1-methyl-piperidine,
cis/trans-3-methoxy-4-(3,4-dimethylphenoxy)-1-methyl-piperidine,
trans-3-hydroxy-4-(3,4-dimethylphenoxy)-1-propargyl-piperidine,
trans-4-hydroxy-3-(3,4-dimethylphenoxy)-1-methyl-piperidine,
trans-3-hydroxy-4-(2-bromo-4-methoxyphenoxy)-1-methyl-piperidine,
cis/trans-3-hydroxy-4-(2,3-dimethylphenoxy)-1-methyl-piperidine,
cis-3-hydroxy-4-(3,4-dimethylphenoxy)-1-methyl-piperidine,
cis/trans-3-hydroxy-4-(1-naphthyloxy)-1-methyl-piperidine,
cis/trans-3-hydroxy-4-(m-chlorophenoxy)-1-methyl-piperidine,
cis/trans-3-hydroxy-4-(5,6,7,8-tetrahydro-1-naphthyloxy)-1-methyl-piperidine,
cis/trans-3-hydroxy-4-(p-fluorophenoxy)-1-methyl-piperidine,
trans-3-acetoxy4-(3,4-dimethylphenoxy)-1-methyl-piperidine,
trans-3-hydroxy-4-(p-trifluoromethylphenoxy)-1-methyl-piperidine,
cis/trans-3-methoxy-4-(2,3-dimethylphenoxy)-1-methyl-piperidine,
1-phenylmethyl-3-methoxy-4-phenylaminopipendine, or
a compound having the formula

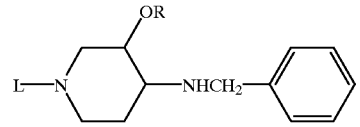

wherein R represents hydrogen or methyl and L is selected from —$CH_2$—Ph, —$(CH_2)_3$—$CH(4F—Ph)_2$, or ethyl, with Ph being phenyl.

2. A compound as in claim 1 wherein R is alkyl, one of $R^1$ and $R^2$ is hydroxy, alkoxy, alkoxyalkoxy, or acyloxy and the other of $R^1$ and $R^2$ is hydrogen, or alkoxy, or $R^1$ and $R^2$ together form —W—$(CH_2)_q$—W'—, wherein W and W' each independently are O, or S and q is 2, or 3; and n, m, X and Ar is as defined in claim 1.

3. A compound of claims 1 or 2 which is
(±)-trans-4-[2-(3,4-Dichlorophenoxy)-ethyl]-3-methoxy-N-pentylpiperidine,
(±)-cis-4-[2-(2,3-Dimethylphenoxy)-ethyl]-3-methoxy-N-pentylpiperidine,
(±)-cis-4-(2-(3,4-Dichlorophenoxy)-ethyl]-3-ethoxy-(2-methoxy)-N-pentylpiperidine,
(±)-tans-4-[2-(3,4-Dichlorophenoxy)-ethyl]-3-ethoxy-(2-methoxy)-N-pentylpiperidine,
(±)-trans-4-[2-(3,4-Dichlorophenoxy)-ethyl]-3-acetoxy-N-pentylpiperidine,
(±)-trans-4-[2-(3-isopropoxyphenoxy) ethyl]-3-(2-methoxy-1-ethoxy)-N-pentylpiperidine,
(±)-trans-4-[4-phenoxyphenoxy]-3-(2-methoxy-1-ethoxy)-N-pentylpiperidine,
(±)-trans-4-[2-(N,N-diphenylamino)ethyl]-3-methoxy-N-pentylpiperidine,
(±)-cis-4-[2-(N,N-diphenylamino)ethyl]-3-methoxy-N-pentylpiperidine, (±)-cis-4-[2-(2-phenylphenoxy)ethyl]-3-methoxy-N-pentylpiperidine, (±)-trans-4-[(4-chlorobenzyl)thio]-3-(2-methoxy-1-ethoxy)-N-pentylpiperidine, (±)-cis-4-[2-(2-benzylphenoxy)ethyl]-3-methoxy-N-pentylpiperidine, (±)-trans-4-[2-(2-benzylphenoxy)ethyl]-3-methoxy-N-pentylpiperidine, (±)-trans-4-[(2-benzyloxyphenoxy)]-3-(2-methoxy-1-ethoxy)-N-pentylpiperidine, (±)-trans-4-[2-(N,N-diphenylamino)ethyl]-3-(2-methoxy-1-ethoxy)-N-pentylpiperidine, or (±)-7-pentyl-10-(2-[4-chlorophenoxy]ethyl)-1,4-dioxa-7-aza-spiro[4,5]decane or a pharmaceutically-acceptable addition salt thereof.

4. A pharmaceutical composition comprising an effective amount of a compound of claims 1, or a pharmaceutically-acceptable addition salt thereof, together with at least one pharmaceutically-acceptable carrier or diluent.

5. A process for the preparation of a compound of claims 1, comprising the step of a) reacting a quinuclidinium salt of formula

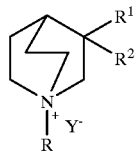

wherein R, $R^1$ and $R^2$ are as defined above in claim 1 and Y is a counter ion, with a compound of the formula HX—$(CH_2)_m$—Ar or a reactive derivative thereof, wherein X, m and Ar is as defined in claim 1, and thereafter optionally forming a pharmaceutically acceptable salt thereof, or b) reacting a compound of formula

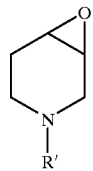

wherein $R^1$ is as defined for R in claim 1, or a protecting group, with a compound of formula HX—$(CH_2)_m$—Ar or a reactive derivative thereof, wherein X, m and Ar is as defined in claim 1, and thereafter optionally i) replacing a protective group with a group R using conventional methods, and/or ii) forming a pharmaceutically acceptable salt thereof.

6. A method of treating a disorder or disease of a living animal body, which disorder or disease is responsive to the partial or complete blockade of calcium channels of the central nervous system comprising the step of administering to such a living animal body, in need thereof a therapeutically effective amount of a compound having the formula

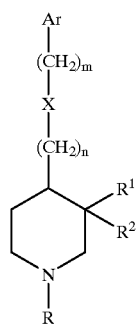

any of its enantiomers or any mixture thereof, or a pharmaceutically-acceptable addition salt thereof, wherein X is O, S, or $NR^3$, wherein $R^3$ is hydrogen, alkyl, or aryl which may be substituted one or more times with substitutents selected from the group consisting of alkyl, alkoxy, halogen, amino, nitro, cyano, trifluoromethyl, aryl, arylalkyl, aryloxy and arylalkyloxy;

m is 0,1, or 2;

n is 0,1, or 2;

R is cycloalkyl, cycloalkylalky, $(aryl)_p$-alkyl, $(aryl)_p$-alkenyl, or $(aryl)_p$-alkynyl, wherein the aryl group may be substituted one or more times with substitutents selected from the group consisting of alkyl, alkoxy, halogen, amino, nitro, cyano and trifluoromethyl, and p is 0, or 1;

one of $R^1$ and $R^2$ is —O—Z, or —S—Z, wherein Z is hydrogen; alkyl; alkenyl; alkynyl; cycloalkyl; cycloalkylalky; arylalkyl, arylalkenyl, arylalkynyl, or aryl-CO—, wherein the aryl groups may be substituted one or more times with substitutents selected from the group consisting of alkyl, alkoxy, halogen, amino, nitro, cyano and trifluoromethyl; or Z is —$(CH_2)_o$—CO—$R^6$, —$(CH_2)_o$—$COOR^6$, —$(CH_2)_o$—$CONR^6R^7$, or —$(CH_2)_o$—Het, wherein o is 0, 1, 2, 3, 4, or 5 and $R^6$ and $R^7$ each independently are hydrogen, or alkyl, and Het is a five or six membered monocyclic heterocyclic ring; or Z is —$(CH_2)_o$—$WR^4$, or

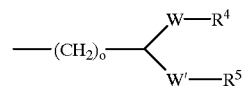

wherein o is 0, 1, 2, 3, 4, or 5, W and W' each independently are O, or S, and $R^4$ and $R^5$ each independently are hydrogen, or alkyl, or wherein $R^4$ and $R^5$ together is —$(CH_2)_q$—, wherein q is 2, or 3; and the other of $R^1$ and $R^2$ is hydrogen, alkoxy, or alkoxyalkoxy; or $R^1$ and $R^2$ together form a chain —W—$(CH_2)_q$—W'—, wherein W and W' each independently are O, or S and q is 2, or 3; and Ar is aryl which may be substituted one or more times with substitutents selected from the group consisting of alkyl, alkoxy, halogen, amino, nitro, cyano, trifluoromethyl, aryl, arylalkyl, aryloxy, and arylalkyloxy;

with the proviso that when m and n are both zero, one of $R^1$, $R^2$ is alkoxyalkoxy and R is an alkylene chain with at least 2 carbon atoms; and with the proviso that said compound is not trans-3-hydroxy-4-(3,4-dimethylphenoxy)-1-methyl-piperidine-hydrochloride, trans-3-hydroxy-4-phenylthio-1-methyl-piperidine,
cis/trans-3-methoxy-4-(3,4-dimethylphenoxy)-1-methyl-piperidine,
trans-3-hydroxy-4-(3,4-dimethylphenoxy)-1-propargyl-piperidine,
trans-4-hydroxy-3-(3,4dimethylphenoxy)-1-methyl-piperidine,
trans-3-hydroxy-4-(2-bromo-4-methoxyphenoxy)-1-methyl-piperidine,
cis/trans-3-hydroxy-4-(2,3-dimethylphenoxy)-1-methyl-piperidine,
cis-3-hydroxy-4-(3,4-dimethylphenoxy)-1-methyl-piperidine,
cis/trans-3-hydroxy-4-(1-naphthyloxy)-1-methyl-piperidine,
cis/trans-3-hydroxy-4-(m-chlorophenoxy)-1-methyl-piperidine,
cis/trans-3-hydroxy-4-(5,6,7,8-tetrahydro-1-naphthyloxy)-1-methyl-piperidine,
cis/trans-3-hydroxy-4-(p-fluorophenoxy)-1-methyl-piperidine,
trans-3-acetoxy-4-(3,4-dimethylphenoxy)-1-methyl-piperidine,
trans-3-hydroxy-4-(p-trifluoromethylphenoxy)-1-methyl-piperidine,
cis/trans-3-methoxy-4-(2,3-dimethylphenoxy)-1-methyl-piperidine,
1-phenylmethyl-3-methoxy-4-phenylaminopiperidine, or
a compound having the formula

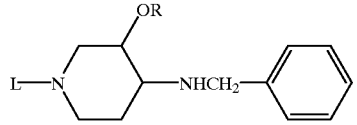

wherein R represents hydrogen or methyl and L is selected from —CH$_2$—Ph, —(CH$_2$)$_3$—CH(4F—Ph)$_2$, or ethyl, with Ph being phenyl.

7. A method as in claim 6 wherein the disorder or disease is stroke, anoxia, ischemia, migraine, psychosis, or epilepsy or a convulsive disorder or degenerative change connected with the above disorders.

8. The method according to claim 6 wherein said living animal body is a human.

* * * * *